(12) United States Patent
Chornenky et al.

(10) Patent No.: US 11,666,775 B2
(45) Date of Patent: Jun. 6, 2023

(54) METHOD AND APPARATUS FOR TREATMENT OF BENIGN PROSTATIC HYPERPLASIA (BPH)

(71) Applicant: Minnesota Medical Physics LLC, Eden Prairie, MN (US)

(72) Inventors: Victor I. Chornenky, Minnetonka, MN (US); Ali Jaafar, Eden Prairie, MN (US)

(73) Assignee: Minnesota Medical Physics LLC, Eden Prairie, MN (US)

(*) Notice: Subject to any disclaimer, the term of this patent is extended or adjusted under 35 U.S.C. 154(b) by 1025 days.

(21) Appl. No.: 16/366,462

(22) Filed: Mar. 27, 2019

(65) Prior Publication Data

US 2019/0299018 A1 Oct. 3, 2019

Related U.S. Application Data

(60) Provisional application No. 62/761,540, filed on Mar. 29, 2018.

(51) Int. Cl.
| | |
|---|---|
| *A61N 2/02* | (2006.01) |
| *A61B 18/18* | (2006.01) |
| *A61N 2/00* | (2006.01) |
| *A61B 18/00* | (2006.01) |
| *A61K 31/00* | (2006.01) |

(52) U.S. Cl.
CPC ............. *A61N 2/02* (2013.01); *A61B 18/18* (2013.01); *A61N 2/004* (2013.01); *A61B 2018/0022* (2013.01); *A61B 2018/00071* (2013.01); *A61B 2018/00547* (2013.01); *A61B 2018/00779* (2013.01); *A61K 31/00* (2013.01)

(58) Field of Classification Search
CPC .......... A61N 2/00; A61N 2/002; A61N 2/004; A61N 2/02; A61N 2/006; A61N 2/008
See application file for complete search history.

(56) References Cited

U.S. PATENT DOCUMENTS

| | | | | |
|---|---|---|---|---|
| 2,897,411 | A * | 7/1959 | Brown | H01F 7/18 361/143 |
| 5,984,854 | A * | 11/1999 | Ishikawa | A61N 2/02 600/9 |
| 6,418,345 | B1 * | 7/2002 | Tepper | A61N 2/02 607/51 |
| 9,486,638 | B2 | 11/2016 | Chornenky et al. | |
| 9,884,199 | B2 | 2/2018 | Chornenky et al. | |
| 11,129,999 | B2 | 9/2021 | Chornenky et al. | |

(Continued)

*Primary Examiner* — Carrie R Dorna
(74) *Attorney, Agent, or Firm* — Skaar Ulbrich Macari, P.A.

(57) ABSTRACT

A method and apparatus for treatment of benign prostatic hyperplasia (BPH) are provided. The method includes providing a set of coils that generate multidirectional pulsed electromagnetic fields in the prostate. The apparatus comprises a power source, an intelligent controller and an applicator positioned in proximity to the prostate and generating multidirectional pulsed fields according to instructions from the controller. The electric component of the electromagnetic fields generated by a PEMF interacts with cells, increases the number of Ata receptors on their membranes and thus enhances the anti-inflammatory actions of the adenosine A2aAR pathway.

10 Claims, 9 Drawing Sheets

(56) References Cited

U.S. PATENT DOCUMENTS

| | | | |
|---|---|---|---|
| 2010/0121131 A1* | 5/2010 | Mathes | A61N 5/0616 600/14 |
| 2012/0172653 A1* | 7/2012 | Chornenky | A61N 2/02 600/14 |
| 2016/0030761 A1* | 2/2016 | Butters | G01N 37/005 600/14 |

* cited by examiner

ମETHOD AND APPARATUS FOR TREATMENT OF BENIGN PROSTATIC HYPERPLASIA (BPH)

PRIORITY

This application claims the priority benefit of U.S. Provisional Application No. 62/761,540, filed on Mar. 29, 2018, which is hereby incorporated herein by reference in its entirety.

FIELD

The invention relates to a method and apparatus for treatment of benign prostatic hyperplasia (BPH). More specifically, the invention relates to methods and apparatus for providing pulsed electromagnetic frequency (PEMF) stimulation for anti-inflammatory and immunosuppressive therapy of BPH.

BACKGROUND

The prostate is a glandular organ of the male reproductive tract. It is positioned around the urethra anterior to the rectum and directly inferior to the bladder. Benign prostatic hyperplasia (BPH) is a benign increase in size of the prostate. BPH involves hyperplasia of prostatic stromal and epithelial cells, resulting in increased resistance to the flow of urine from the bladder. As BPH progresses it leads to the development of hypertrophy, instability, or weakness of the bladder muscle. Untreated BPH may lead to urinary tract infections, acute urinary retention and kidney and bladder stones.

The hyperplasia of the prostate gland develops as a strictly age-related phenomenon in nearly all men, starting at approximately 40 years of age. The histologic prevalence of BPH is approximately 10% for men in their 30s, 20% for men in their 40s, reaches 50% to 60% for men in their 60s, and is 80% to 90% for men in their 70s and 80s; in 40-50% of these men, BPH becomes clinically significant. In the United States BPH is one of the most prominent and costly diseases in men older than 50 years of age. In the United States alone, BPH is the reason for almost 400,000 hospitalizations per year. Direct and indirect annual costs of BPH treatment in the U.S. are estimated to be more than 4 billion dollars annually.

The treatment options for patients suffering from BPH are medications and/or invasive therapy. Available drug therapies for BPH fall under two general categories: alpha-blockers and 5 alpha-reductase inhibitors, both of which can improve urine flow, but they do not reduce the size of the prostate and can contribute to sexual dysfunction or hypotension as side effects. The examples of these medications are finasteride (Proscar), doxazocin (Cardura), tamsulosin (Flomax) and others. Different drugs affect the disease in different ways, but all of them do not fulfil expectations. A satisfactory improvement of the symptoms and the functional impairments has not yet been achieved.

Invasive interventions such as TURP (Transurethral Resection of the Prostate) or balloon dilatation are used in treatment of BPH. TURP refers to a method in which, starting from the urethra, the prostate is resected. Removing the proliferating prostate tissue reduces the compression of the urethra and relives symptoms. The same therapeutic effect is achieved with balloon dilatation. In comparison with TURP, balloon dilatation treatment involves a high recidivity rate and requires repeated treatments. Both methods cause heavy strain for the patients. TURP, in particular, has a high morbidity rate, with the prime factors being hemorrhages and trauma. In some cases, patients are hospitalized for long periods of time, causing high costs for the treatment. TURP-treated patients often suffer from urethra strictures which also have to be treated. The most serious side effects of TURP are impotence and erectile dysfunction caused by damage to sensitive nerve threads. This has been the reason for intensive research into additional and enhanced therapies.

Recent increasing evidence supports the idea that BPH comprises an inflammatory-based disorder. Inflammation is initiated by an unknown stimulus that creates a proinflammatory milieu within the gland. This theory is confirmed by several basic research and clinical studies that showed a statistically significant association between inflammation and BPH severity and progression. From these clinical and basic studies a novel approach to the clinical management of BPH has been developed. This approach takes into account an important role of inflammatory and autoimmune processes in BPH pathology. The main characteristic of this inflammatory process is the absence of bacterial or viral pathogens. Recent studies support the hypothesis that, in the case of BPH, the inflammatory changes are a consequence of misdirected and excessive immune response. Certain components of the prostate secretion which attract immunoreactive CD4+ T-cells might be the cause. The establishment of reactive T-cells and production by cells of the connective tissue stimulatory cytokines increases the reactivity of T-cells. These cytokines such as IFN-gamma, IL-2 and TGF-beta are capable of stimulating the proliferation of smooth muscle cells and epithelial cells. This process is, in many aspects, similar to the process of cicatrisation. Here also, cytokines stimulate tissue growth. In contrast to the process of a scar cicatrizing, the pathologic immunoreaction of BPH and the resulting tissue proliferation persist. An effective therapy focused on this mechanism of the disease has not been known and has not been available. With view to recent research results, however, a causal therapy should prevent misdirected and excessive pathological immunoreactions in prostate tissue.

Adenosine is a purine nucleoside generated by metabolically stressed or inflamed tissues that is recently recognized as a major endogenous anti-inflammatory regulator. Under normal conditions, adenosine is continuously released from cells as a product of ATP degradation. Adenosine concentration in extracellular space is controlled by an enzyme called adenosine deaminase (ADA) which breaks it down and keeps the concentration level in a low-micromolar to a high-nanomolar range. However, during conditions of stress, such as hypoxia during inflammation, levels of extracellular adenosine rise dramatically (up to 200-fold). This is partly due to increased production of AMP in hypoxic conditions, but substantial amounts of adenosine are also produced by the platelets and hematopoietic cells, as well as damaged cells. Adenosine regulates the function of the innate and adaptive immune systems through targeting virtually every cell type that is involved in orchestrating the immune/inflammatory response. Of the four adenosine receptors (A1, A2a, A1b, A3), A2a receptors have taken center stage as the primary anti-inflammatory effectors of extracellular adenosine. This broad, anti-inflammatory effect of A2a receptor activation is a result of the predominant expression of A2a receptors on monocytes/macrophages, dendritic cells, mast cells, neutrophils, endothelial cells, eosinophils, epithelial cells, as well as lymphocytes, NK cells, and NKT cells. A2a receptors play a critical role in controlling leukocyte trafficking by suppressing release of cytokines that induce production of adhesion molecules (ICAM-1/VCAM-1) and promote the "roll", "stop" and "exit" mechanism bringing lymphocytes from blood vessels into tissues.

A2a receptor activation inhibits early and late events occurring during an immune response, which include immune cell trafficking, immune cell proliferation, proinflammatory cytokine production, and cytotoxicity. In late stages of inflammation, in addition to limiting inflammation, A2a receptors participate in tissue remodeling and restoration. Consistent with their multifaceted, immunoregulatory action on immune cells, A2a receptors have been shown to positively impact the course of a wide spectrum of ischemic, autoimmune, infectious, and allergic diseases.

Pulsed Electromagnetic Field Therapy (PEMF) is a new non-invasive method of treatment of numerous medical conditions related to injuries and inflammations of different tissues: bones, cartilages, soft and neurological tissues. For centuries it was common knowledge that natural wound healing involves generation of endogenous electric fields. Recently it has been discovered that the endogenous electric fields also control the processes of remodeling and healing bones and cartilages.

In PEMF therapy the electric field is carried into the treatment zone by a pulsed magnetic field produced by electromagnetic coils from outside the body. A PEMF system applies a series of magnetic pulses to injured tissue where each magnetic pulse induces an electrical signal that stimulates cellular anti-inflammatory and anabolic activities. PEMF therapy reduces pain associated with inflammation by suppressing production of pain mediator prostaglandin E2 and accelerates natural healing of tissues. Multiple studies have demonstrated effectiveness and safety of PEMF therapy in suppressing inflammation.

Recently it has been established by Varani et al. that the anti-inflammation mechanism by action of PEMF on a cell is due to its ability to increase the concentration of receptors A2a on the cell membrane. PEMF stimulation increases the number of active A2a receptors on the cell membrane by creating a conformational change of their protein and making them active and available for binding with adenosine ligand. The strength of the signal to the cell and the biological response of the cellular machinery depend on both the concentration of ligands in the extracellular space and the concentration of receptors on the cell membrane. As a result, the same anti-inflammation response can be achieved by two different ways: by changing concentration of adenosine around the cell and by changing concentration of the receptors on the cell membrane. The essence of the discovery by Varani et al. is that the adenosine signaling pathway can be up-regulated without changing extracellular adenosine concentration, with PEMF stimulation alone.

According to experimental data, the A2a receptors can be up-regulated by the pulsed electric fields with amplitude above 50 µV/cm. In the environment rich in extracellular adenosine, which is always the case with inflamed or stressed tissues, the up-regulation of A2a receptors leads to significant amplification of adenosine signaling. PEMF stimulation triggers the same physiological response of the cell as a local increase in concentration of adenosine or another A2a agonist. In either case the magnitude of signal from A2a receptors to the cellular machinery increases along with the downstream effects of the A2a signaling.

PEMF stimulation can affect a wide variety of cells that express A2a receptors, including T cells, macrophages, neutrophils and other lymphocytes. All parenchymal prostate cells express A2a receptors and can be stimulated by PEMF. A2a receptor signaling amplified by PEMF is able to inhibit multiple processes occurring during an immune response, including immune cell trafficking and proliferation, pro-inflammatory cytokine production and cytotoxicity. In addition to limiting inflammation, A2a receptors participate in tissue remodeling and repair. A2a receptors have been shown to impact the course of autoimmune, infectious, and allergic diseases. PEMF stimulation of A2a receptors generates immunosuppressive action by inhibiting overreactive immune cells, thereby protecting tissues from collateral inflammatory damage. PEMF stimulation of A2a receptors provides a novel regulatory tool for immune/inflammatory diseases of various organs, including prostate. They can be a critical part of the physiological negative feedback that limits local chronic inflammatory responses. Increased by PEMF stimulation, A2a signaling inhibits development of cytotoxicity and cytokine-producing activity of T-cells. Stimulated by PEMF, the A2a receptors in autoreactive T-cells generate strong immunosuppressive action that reduces chronic inflammation and subsequent damage to the affected organ. Thus, there is a continuing need to develop efficient BPH using PEMF.

SUMMARY

The objective of certain embodiments of the invention is to provide a noninvasive method of treatment of BPH comprising anti-inflammatory PEMF stimulation. Another objective of certain embodiments is to provide an apparatus for anti-inflammatory treatment of BPH utilizing PEMF stimulation.

A method and apparatus for treatment of benign prostatic hyperplasia (BPH) are provided. The method includes providing a set of coils that generate multidirectional pulsed electromagnetic fields in the prostate. The apparatus comprises a power source, an intelligent controller and an applicator positioned in proximity to the prostate and generating multidirectional pulsed fields according to instructions from the controller. The electric component of the electromagnetic fields generated by a PEMF interacts with cells, increases the number of A2a receptors on their membranes and thus enhances the anti-inflammatory actions of the adenosine A2aAR pathway.

Provided in one example is a PEMF stimulation apparatus for treatment of BPH. The apparatus can comprise an applicator and a controller. The applicator can include a first coil provided to the applicator and a double pole double throw switch coupled to the first coil. The controller can be coupled to the first coil and configured to actuate the switch to periodically switch directions of an electric current in the first coil during a treatment regimen.

The applicator can be configured as a seat cushion that can be sat upon by a patient during the treatment regimen. The applicator can be configured as a cushion that defines a central channel in which the first coil is disposed.

A second coil can be disposed adjacent to the first coil to define a first linear axis between the first and second coils. A third coil and a fourth coil can also be provided to the applicator. The third and fourth coils define a second linear axis between the third and fourth coils. The second linear axis can be perpendicular to the first linear axis.

A free wheel diode can be connected parallel to the first coil. The first coil can comprise several turns of wire that are embedded within a ceramic pad.

The controller can include a display screen and an on/off actuator.

Also provided is a method of treating BPH in a patient that includes providing PEMF stimulation to a patient's prostate to increase a number of active Ata receptors on cell membranes of the patient's prostate.

PEMF stimulation can be provided by an applicator placed adjacent to a perineum of the patient. The patient can sit on the PEMF applicator during a treatment regimen.

The PEMF stimulation can be provided by a plurality of coils disposed in an applicator. The plurality of coils can comprise two coils disposed adjacent to one another to define a linear axis between the two coils. The plurality of coils can also comprise four coils. If four coils, then two of the coils are disposed adjacent to one another to define a first linear axis between the first two coils, and a second two of the four coils are disposed adjacent to one another to define a second linear axis between the second two coils that is perpendicular to the first linear axis.

The coil or coils can be coupled to a controller to periodically switch directions of an electric current in each of the coils during a treatment regimen.

The PEMF delivery circuit can be protected from voltage spikes arising during a switching off of current pulses in a PEMF coil by connecting a free wheel diode in parallel to the PEMF coil.

The PEMF stimulation can be provided by an applicator comprising a coil disposed inside of a cushion, wherein the coil comprises several turns of wire that is embedded within a ceramic pad. The cushion can define a central channel in which the coil is disposed. If multiple coils, then the cushion can define a central channel in which the coils are disposed along two intersecting axes.

A remaining time of treatment can be displayed on a display screen of a controller coupled to a PEMF stimulation applicator.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
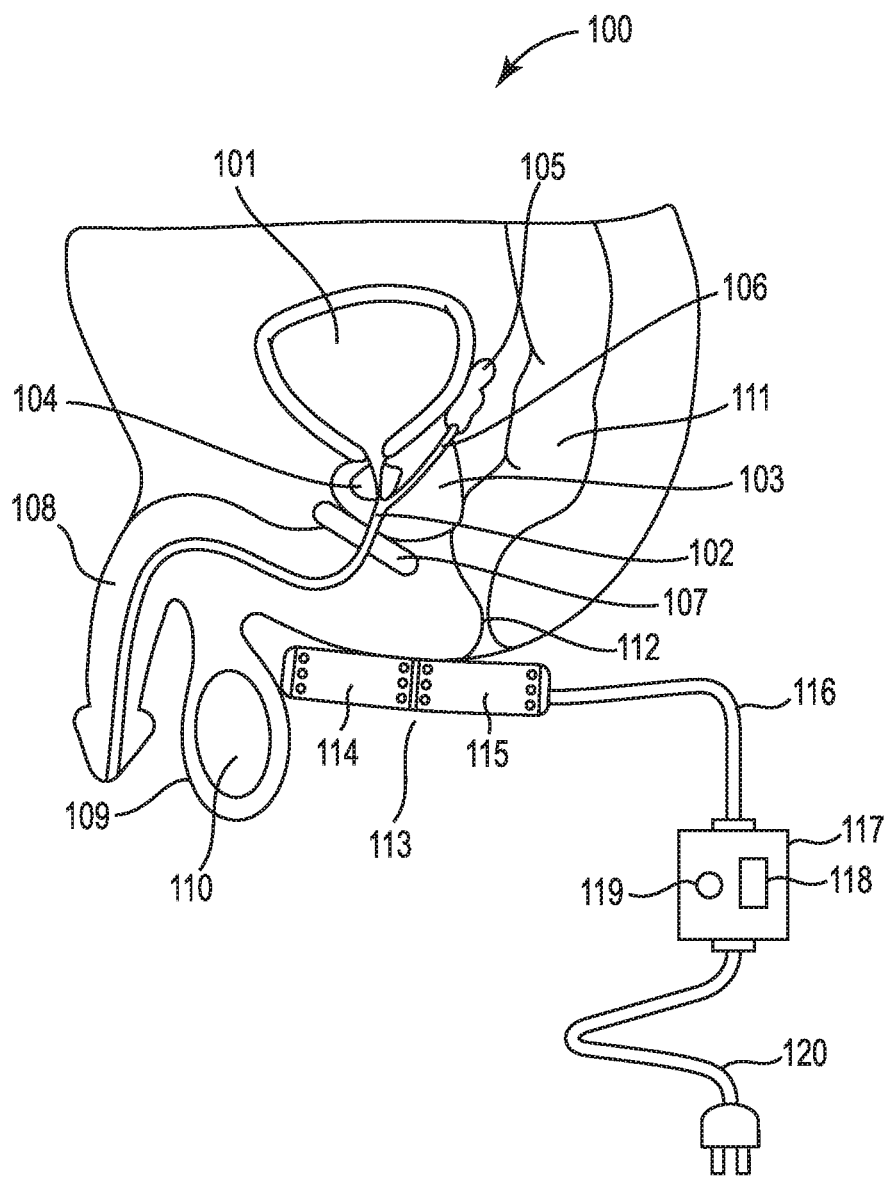
FIG. 1 is a schematic illustration of the prostate and apparatus for treatment of BPH according to certain embodiments.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

In FIG. 1 an apparatus for treatment of BPH 100 is schematically shown. Numeral 101 designates the patient's bladder and 102 designates the urethra fluidly connected to the bladder 101 and to the outside of the patient's body. Numeral 103 is the prostate gland. Numeral 104 designates the prostate transition zone which may pinch the urethra as symptoms of BPH are progressing. Numeral 105 designates the seminal vesicles communicating with urethra 102 via duct 106. Numeral 107 is the urinary sphincter positioned around urethra 102 between prostate 103 and the distal end of penis 108. Numeral 109 is the patient's scrotum with testicle 110. Numeral 111 designates the colon and 112 the anus.

Applicator 113 of the treatment apparatus 100 comprises electromagnetic coils 114 and 115. Numeral 116 is the multiple wire cable connecting applicator 113 with intelligent controller 117. Numeral 118 designates a display provided to the controller portion. The display 118 indicates information such as remaining time of treatment. An on-off knob 119 is also provided to the controller portion 117. A power supply cable 120 provides power input to the controller 117 and the connected applicator 113.

In use, the applicator 113 is placed between the patient's scrotum 109 and anus 112, so when the patient is seated, his perineum touches the applicator 113.

Figure 2:
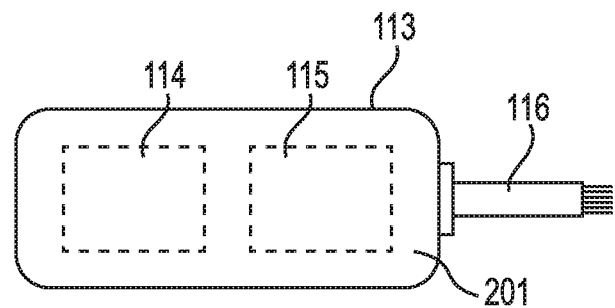
FIG. 2 is a side view of a PEMF applicator for treatment of BPH.

In FIG. 2, applicator 113 is schematically shown. The applicator 113 comprises a flat cushion-shaped body 201 comprising a soft fabric with two electromagnetic coils 114 and 115 disposed inside of the fabric. Cable 116 connects the applicator 113 to the intelligent controller 117 that was shown in FIG. 1. In alternative embodiments, the applicator may be configured with only one coil, or more than two coils.

Figure 3:
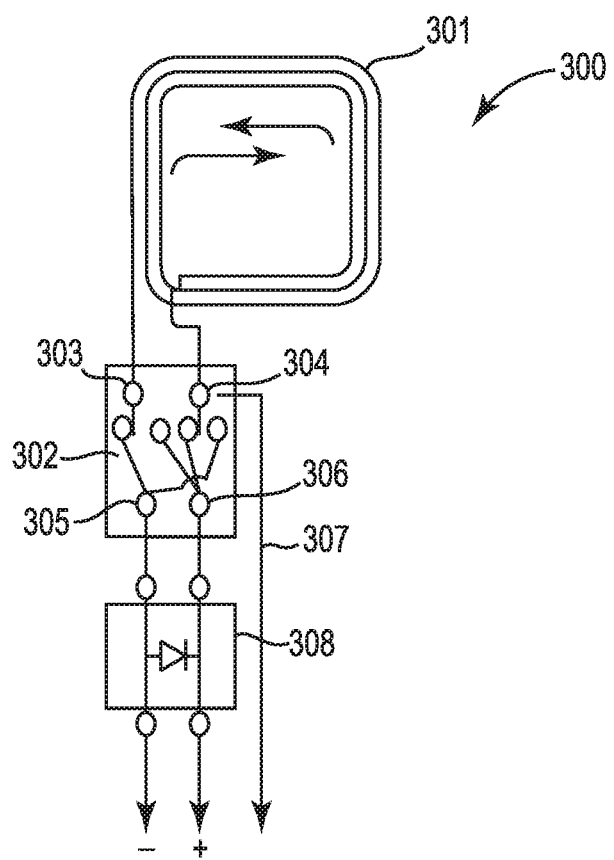
FIG. 3 is an electrical diagram for a switching direction of the electric current in a coil.

FIG. 3 schematically depicts coil assembly 300, which comprises electromagnetic coil 301 coupled to a "double pole double throw" switch 302. The function of the switch 302 is to periodically switch directions of the electric current in coil 301. In one state of the switch 302, contacts 303 and 304 are connected to contacts 305 and 306 respectively and the electric current in the coil 301 is flowing in the counter clock direction. In the second state of the switch 302, the coil contact 303 is connected to contact 306 while contact 304 is connected to contact 305. In this state of the switch 302, the electric current through the coil flows in clockwise direction. Numeral 307 designates a conductor controlling the switching switch 302 between the two states via commands from intelligent controller 117 (not shown in FIG. 3). A "free wheel" diode 308 is connected parallel to the coil 301 and intended to protect coil 301 and the whole circuitry from voltage spikes arising during switching off the current pulses in the coil 301.

Figure 4:
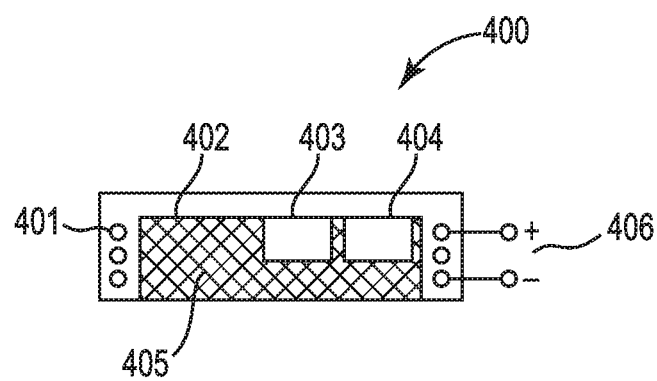
FIG. 4 is a cross-section view of a PEMF applicator according to certain embodiments.

In FIG. 4 a coil assembly 400 is schematically depicted. Numeral 401 designates an electromagnetic coil formed of several turns of 1.5-2.0 mm diameter copper wire imbedded into a ceramic pad 402. Numerals 403 and 404 are the "double pole double throw" switch and "free wheel" diode, respectively, secured to the ceramic pad 402 with ceramic-based glue. Numeral 405 is a potting compound preferably comprising silicone resin, which provides additional electrical insulation to the coil assembly 400. Numeral 406 designates electrical wires connecting the coil assembly 400 to the controller (117 in FIG. 1).

FIGS. 5A-5B and FIGS. 6A-6D schematically illustrate spatial distributions of magnetic fields B(t) and electric fields E(t) for different directions of current pulses through coils 1(t).

Figures 5A, 5B:
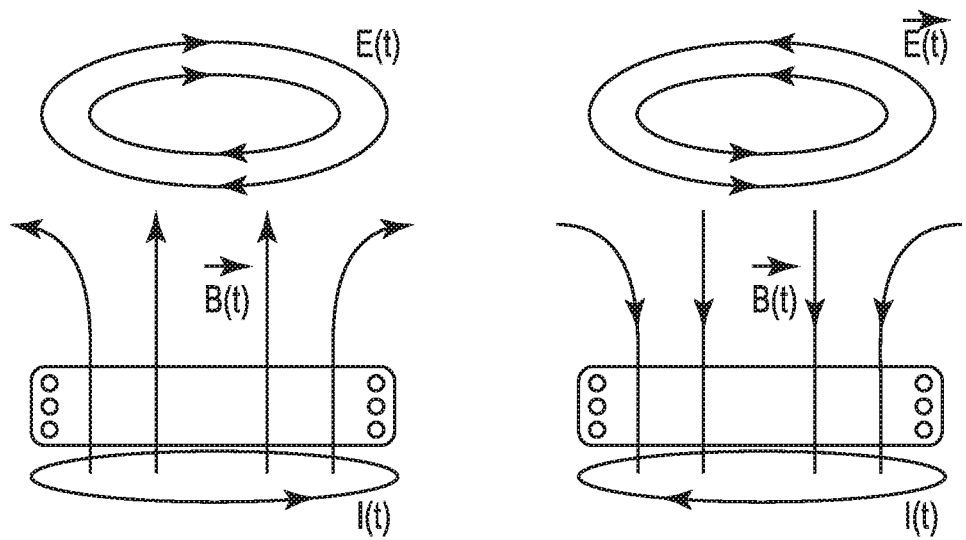
FIGS. 5A and 5B are schematic illustrations of electric current, magnetic and electric fields during PEMF stimulation with a one-coil applicator.

FIGS. 5A-5B illustrate the spatial aspect of electromagnetic stimulation of the prostate with a one coil applicator, with each of the two figures showing stimulating pulsed of E(t) with opposite directions of the currents 1(t) in the coil. The stimulating electric field E(t) is made by locked lines lying in a plane parallel to the plane of the coil.

Figure 6A:
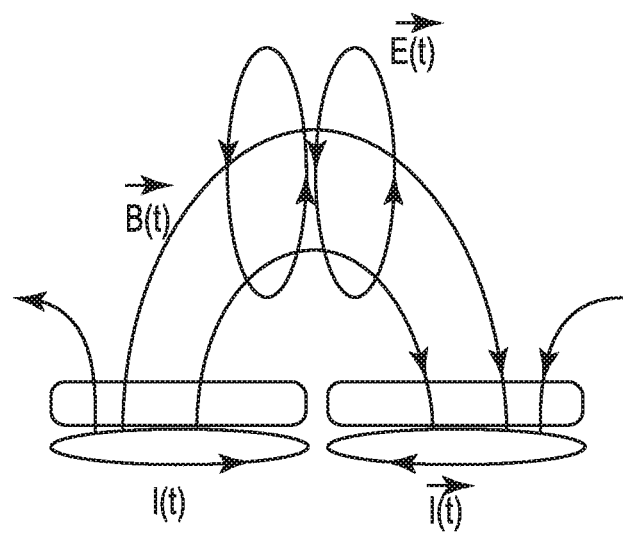
FIGS. 6A, 6B, 6C and 6D are schematic illustrations of electric currents, magnetic and electric fields during PEMF stimulation with a two-coil applicator.
Figure 6B:
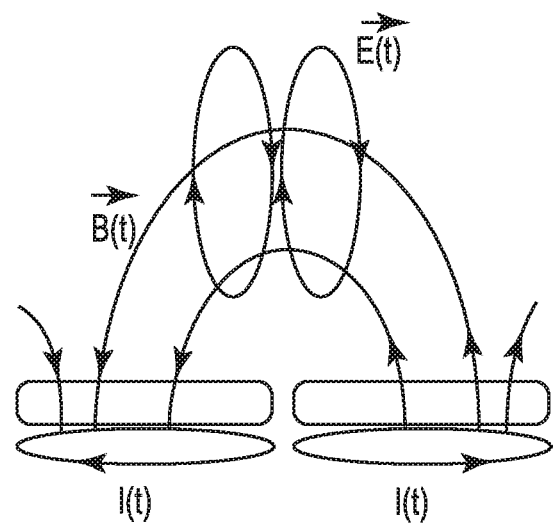
Figure 6C:
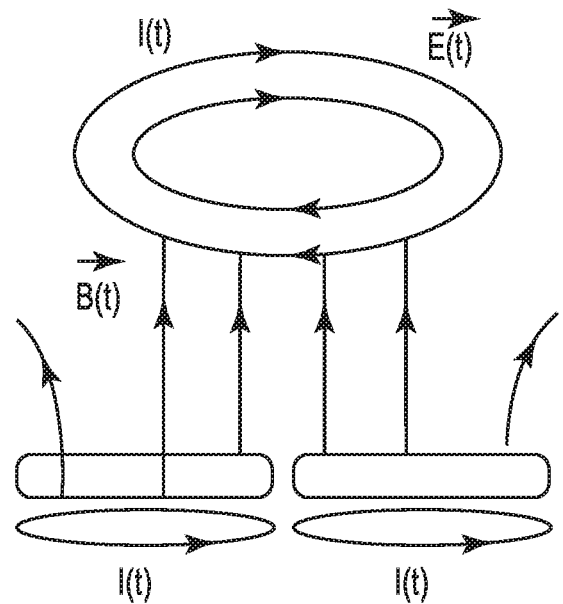
Figure 6D:
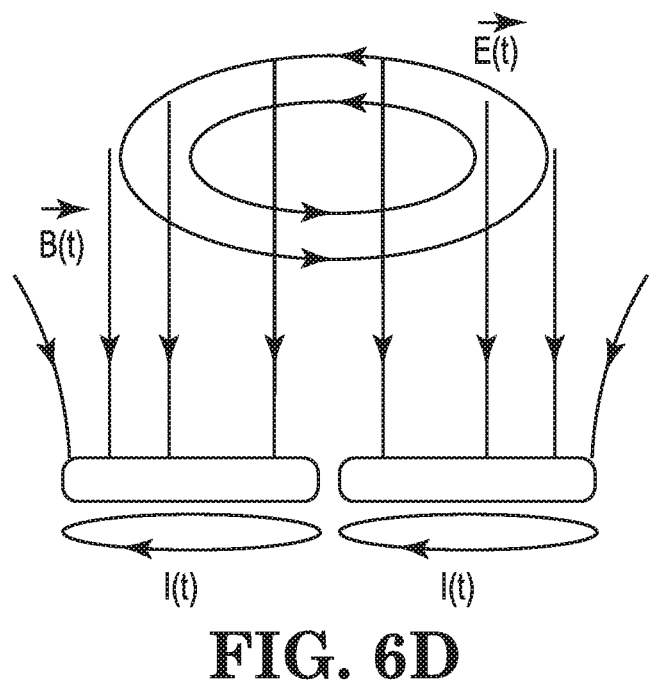

FIGS. 6A-6D illustrate spatial distribution of stimulating electric field E(t) in the treatment area with two-coil applicator. FIGS. 6A-6B show distribution of magnetic field B(t) and electric field E(t) in the case when the electric currents have opposite directions in the coils, whereas FIGS. 6C and 6D depict fields B(t) and E(t) in the case when the currents in coils have the same directions. For the same directions of the currents the electric field lines lie in the plane parallel to the plane of the coils similar to that in FIGS. 5A-5B. For the opposite directions of the currents the stimulating electric field lines E(t) in the treatment zone are laying approximately in a plane perpendicular to the plane of the coils.

During a treatment session, controller 117 provides continuous sequence of pulses of one polarity to each coil of the applicator 113. From time to time with an interval of 10 seconds to 5 minutes, the polarity changes for the pulses in one or both coils. In case of a one coil applicator, this creates two electric field patterns with opposite directions of the electric field in the treatment area, as illustrated by FIGS. 5A-5B. Both patterns are made of electric field lines locked on themselves and positioned horizontally (parallel to the plane of coil).

In the case of a two coil applicator, this creates four different patterns of the electric fields as illustrated by FIG. 6. When currents in both coils of the applicator are of the same direction, the patterns of the electric fields in the treatment area are similar to that of one coil applicator as is in FIGS. 6C-6D. When the current is of opposite directions the electric field lines are positioned vertically as shown in FIGS. 6A-6B.

Figure 7:
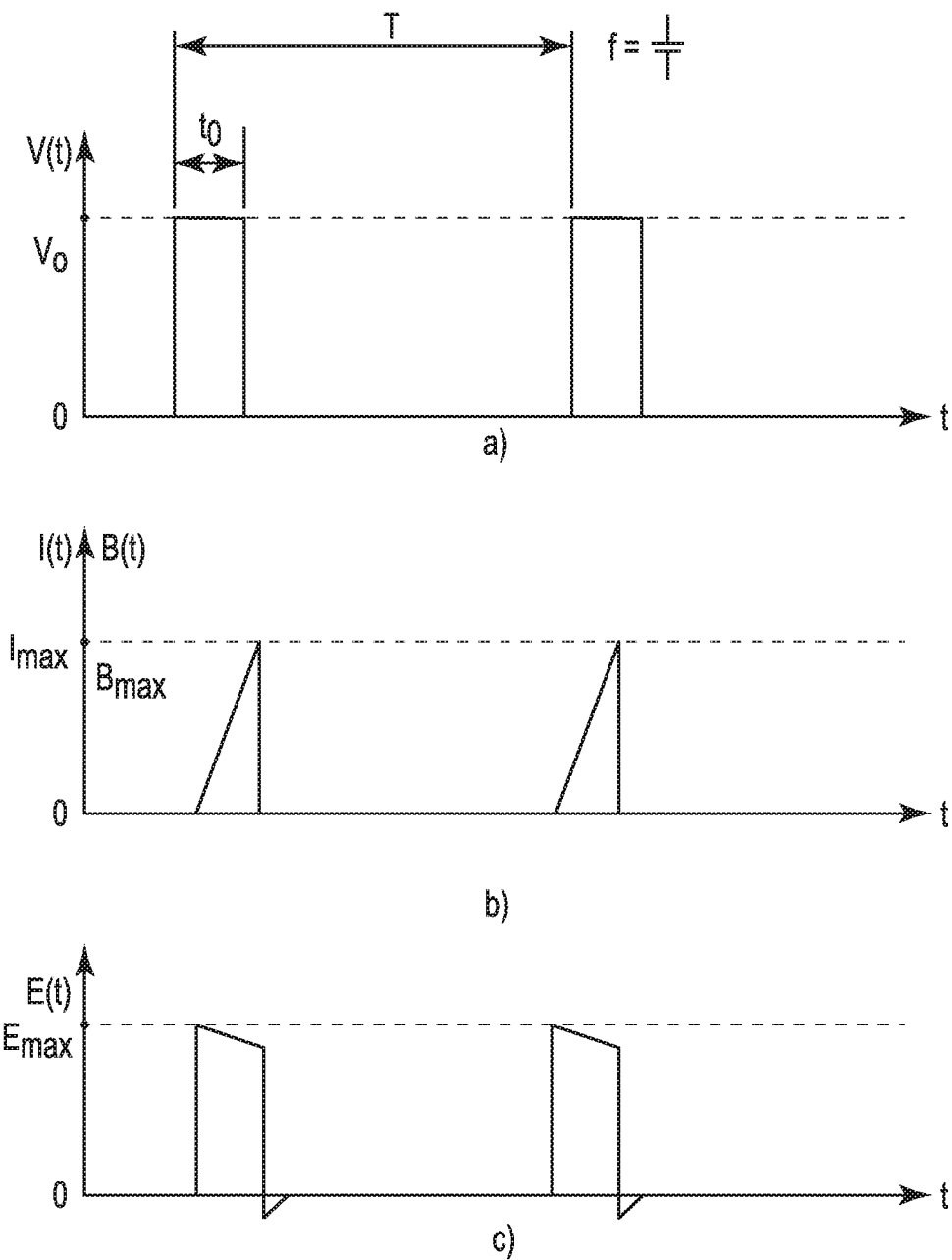
FIG. 7 is a series of three time diagrams showing pulsed electric current, magnetic and electric fields during anti-inflammatory PEMF stimulation.

In FIG. 7, the temporal aspect of stimulation of the prostate is schematically shown. FIG. 7 at graph (a) is a time diagram of voltage applied to the coils. Controller 117 supplies the coils of stimulator (applicator) 113 with a series of rectangular pulses. The pulses may have amplitude $V_0$ ranging from 24V to 250V, duration to between 5 µs to 1000 µs and frequency f (f=1/T) from 10 Hz to 250 Hz, where T is the period between two consecutive series of pulses.

In diagram (b) of FIG. 7, the electric current I(t) and the magnetic field B(t) in coils are shown. An exemplary value of maximum current $I_{max}$ is 200 A to 1000 A and a value of magnetic inductance lies in the range of 1 to 50 milliTesla. The diagram represents ascending exponential curves close in shape to a straight line.

Diagram (c) of FIG. 7 depicts pulsed electric field in the treatment zone with amplitude $E_{max}$ equal to 5-20 mV/cm.

In all cases the current I(t) is approximately a linear function of time for most of the pulse. At the end of the linear phase of the pulse the voltage on the coil is turned off by the controller and the current falls to zero. To avoid voltage spikes after turning off the voltage the current is redirected to the free wheel diode which makes with the coil a locked circuit and thus the current decreases slowly. At the beginning of a pulse the current I(t) in the coil creates a changing magnetic field B(t) which, in turn, creates a curl electric field E(t) around the coil and in the treatment area—the patient's prostate.

Each pattern of the electric field shown in FIGS. 5A-5B and FIGS. 6A-6D leads to activation of adenosine A2a receptors on different parts of membranes of parenchymal cells and immune cells in the treatment zone of the prostate. The electric field activates A2a receptors on one part of the cellular membrane that is normal to the electric field. A two-coil applicator creates more different directions of activation and thus delivers a higher number of A2aARs on the cells' surfaces. The two-coil applicator is preferred for this reason.

Figure 8:
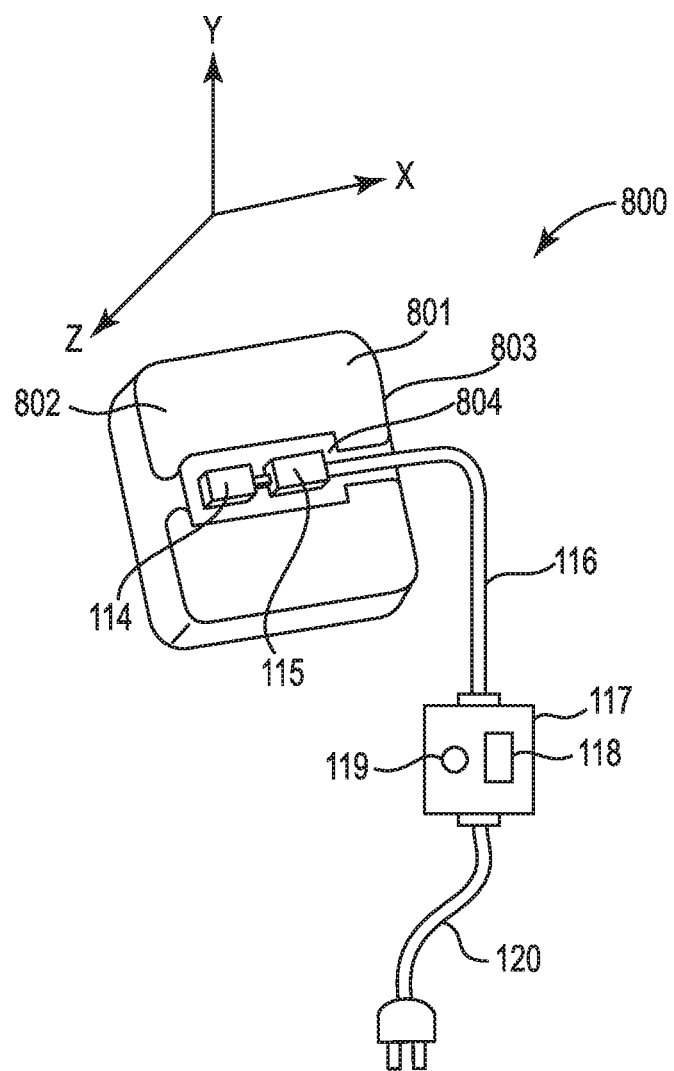
FIG. 8 is a perspective view of an apparatus for treatment of BPH with a two-coil applicator according to certain embodiments.

In FIG. 8, the apparatus 800 for treatment of BPH is schematically shown. Numeral 801 designates a cushion applicator on which a patient is seated during treatment. Cushion applicator 801 has a front side 802 that the patient contacts and a rear side 803 that is opposite the front side. The middle of the cushion 801 defines an elongated channel 804 in which coils 114 and 115 are secured along axis X parallel to the front side surface. Placed in the channel 804 the cable 116 connects coils 114 and 115 with the intelligent controller 117, which, in turn, is plugged in the power outlet via cable 120. Numeral 118 designates the display of the controller 117. An on-off button 119 is also provided to the controller 117.

Figure 9:
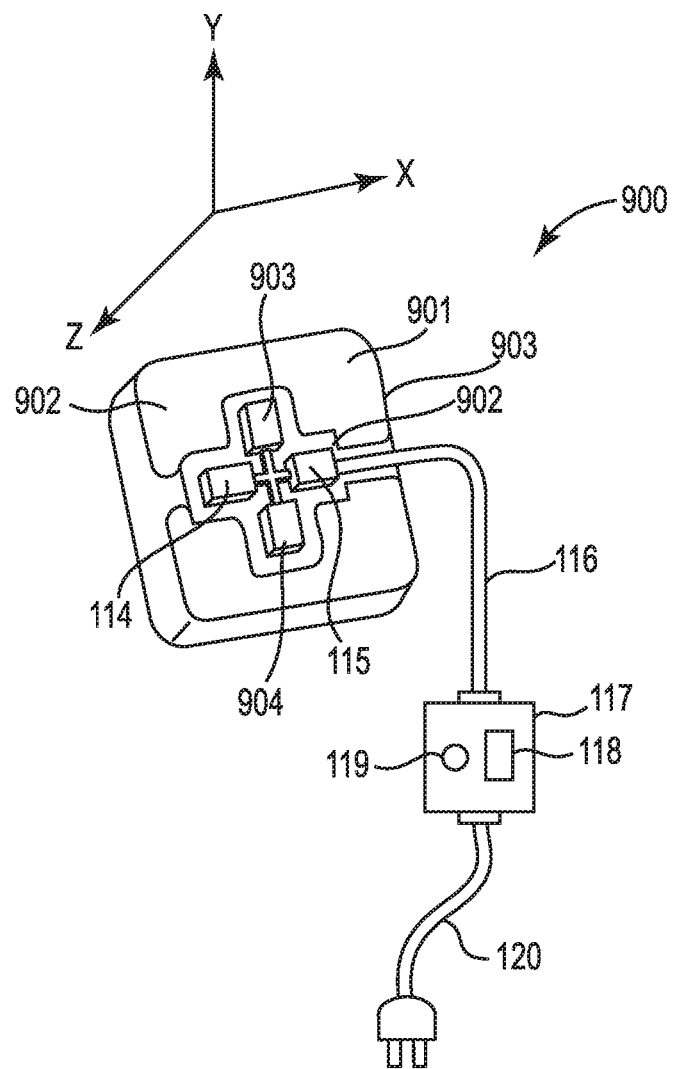
FIG. 9 is a perspective view of an apparatus for treatment of BPH with a four-coil applicator according to certain embodiments.

FIG. 9 illustrates another embodiment of the treatment apparatus 900. In this embodiment the channel 902 in cushion 901 is enlarged transversely as compared to the channel of FIG. 8 to accommodate additional coils. Additional coils 903 and 904 are placed along axis Y perpendicular to the X-axis alignment of coils 114 and 115.

Figure 10A:
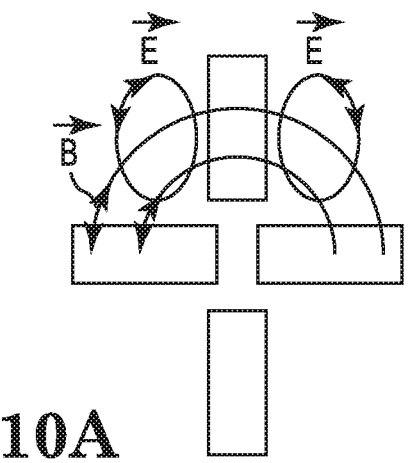
FIGS. 10A, 10B and 10C are schematic illustrations of electric current, magnetic and electric fields during PEMF stimulation with a four-coil applicator.
Figure 10B:
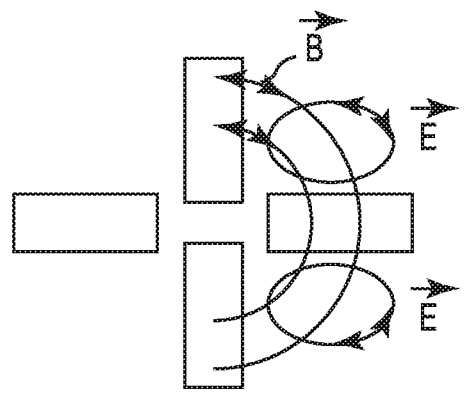
Figure 10C:
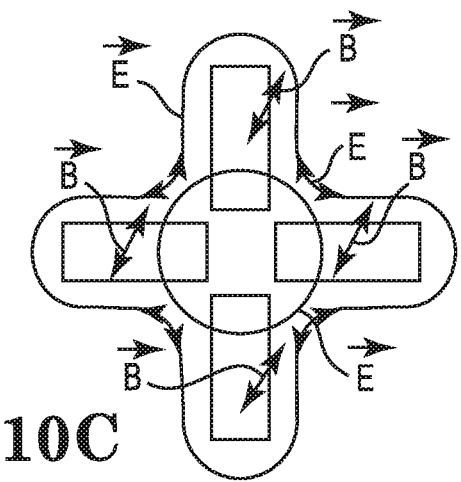

Generated magnetic fields B and electric fields E for this four-coil treatment device 900 are illustrated in FIGS. 10A-10C. Consecutive pulses provided by controller 117 to coils 114, 115, 903 and 904 generate 6 differently oriented magnetic fields B and electric field E along axes X,Y and Z in their positive and negative directions. These electric fields provide multidirectional highly intense PEMF stimulation of the prostate with maximum therapeutic effect on BPH.

Electric field is a vector. During stimulation significant interaction of the electric field with the cellular membrane occurs only in two spots at the apexes of the cell where the electric field is normal the membrane. The time of electrical relaxation of a cell is about 1 µs. After this time the applied electric field is pushed out of the cell and concentrates in two parts of membrane normal to electric field where the field rises to the value of 10 V/cm, which is 1000 times higher than the applied field. From these two spots only one has the right direction of the electric field that causes translocation of A2aARs to the outside surface of the cell. So, only one spot of the membrane contributes to enhancement of adenosine—A2aAR anti-inflammatory pathway during a particular stimulation direction. On the other hand, in the parts of the cell's membrane that are parallel to the applied electric field the value of the electric field did not change, and so the number of the receptors did not change. No contribution to upregulation of adenosine—A2aAR signaling pathway occurred from these parts of the membrane. Stimulating a cell with multiple directions of electric field allows covering the membrane with multiple spots with increased numbers of active A2aARs, and thus achieve maximum therapeutic effect.

It is also within the scope of the invention to combine features, functions, advantages and aspects of the various embodiments described herein. Thus, the embodiments of the invention may comprise combinations of aspects of any one or more of these exemplary embodiments.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A pulsed electro-magnetic field (PEMF) stimulation apparatus for generating multidirectional pulsed electric field stimulation of the prostate in order to treat benign prostatic hyperplasia (BPH), the apparatus comprising:
   an applicator, comprising:
      a first coil provided to the applicator;
      a second coil provided to the applicator;
      a first double pole double throw switch coupled to the first coil;
      a second double pole double throw switch coupled to the second coil;
      a first free wheel diode connected parallel to each pole of the first double pole double throw switch;
      a second free wheel diode connected parallel to each pole of the second double pole double throw switch,
      wherein the applicator is configured as a seat cushion that can be sat upon by a patient undergoing a treatment regimen for BPH, and
      wherein the first coil and second coil are arranged in the applicator such that the multidirectional pulsed electric field stimulation generated by the first and second coils treats a patient's prostate; and
   a controller coupled to the first coil and the second coil, the controller configured to:
      provide a continuous train of electrical pulses to the first and second coils via the respective first and second double pole double throw switches;
      actuate periodically the first and second double pole double throw switches to switch directions of one or more electrical pulses in the train of electrical pulses in each of the first and second coils in a predetermined sequence to generate the multidirectional pulsed electric field stimulation of the patient's prostate during the treatment regimen for BPH.

2. The apparatus of claim 1, wherein the second coil is disposed adjacent to the first coil to define a first linear axis between the first and second coils.

3. The apparatus of claim 2, further comprising a third coil and a fourth coil provided to the applicator, wherein the third and fourth coils define a second linear axis between the third and fourth coils, wherein the second linear axis is perpendicular to the first linear axis.

4. The apparatus of claim 1, wherein the first coil and the second coil each comprise several turns of wire that are embedded within a ceramic pad.

5. The apparatus of claim 1, wherein the controller includes a display screen and an on/off actuator.

6. A pulsed electro-magnetic field (PEMF) stimulation apparatus for generating multidirectional pulsed electric field stimulation of the prostate in order to treat benign prostatic hyperplasia (BPH), the apparatus comprising:
   an applicator, comprising:
      a first coil provided to the applicator;
      a second coil provided to the applicator;
      a third coil provided to the applicator;
      a fourth coil provided to the applicator;
      a first double pole double throw switch coupled to the first coil;
      a second double pole double throw switch coupled to the second coil;
      a third double pole double throw switch coupled to the third coil;
      a fourth double pole double throw switch coupled to the fourth coil;
      a first free wheel diode connected parallel to each pole of the first double pole double throw switch;
      a second free wheel diode connected parallel to each pole of the second double pole double throw switch;
      a third free wheel diode connected parallel to each pole of the third double pole double throw switch,
      a fourth free wheel diode connected parallel to each pole of the fourth double pole double throw switch,
      wherein the applicator is configured as a seat cushion that can be sat upon by a patient undergoing a treatment regimen for BPH, and
      wherein the first, second, third and fourth coils are arranged in the applicator such that the multidirectional pulsed electric field stimulation generated by the first, second, third and fourth coils treats a patient's prostate; and
   a controller coupled to each of the first, second, third and fourth coils, the controller configured to:
      provide a continuous train of electrical pulses to the first, second, third and fourth coils via the respective first, second, third and fourth double pole double throw switches;
      actuate periodically the first, second, third and fourth double pole double throw switches to switch directions of one or more electrical pulses in the train of electrical pulses in each of the first, second, third and fourth coils in a predetermined sequence to generate the multidirectional pulsed electric field stimulation of the patient's prostate during the treatment regimen for BPH.

7. The apparatus of claim 6, wherein the first and second coils define a first linear axis between the first and second coils.

8. The apparatus of claim 7, wherein the third and fourth coils define a second linear axis between the third and fourth coils, wherein the second linear axis is perpendicular to the first linear axis.

9. The apparatus of claim 6, wherein the controller includes a display screen and an on/off actuator.

10. The apparatus of claim 6, wherein the first, second, third and fourth coils each comprise several turns of wire that are embedded within a ceramic pad.

* * * * *